(12) United States Patent
Chabbert et al.

(10) Patent No.: US 8,580,730 B2
(45) Date of Patent: Nov. 12, 2013

(54) METHODS OF TREATING LESIONAL VESTIBULAR DISORDERS BY ADMINISTERING SEROTONIN 5-HT3 RECEPTOR ANTAGONISTS

(75) Inventors: Christian Chabbert, Montpellier (FR); Frederic Venail, Montpellier (FR)

(73) Assignee: (INSERM) Institut National de la Sante et de la Recherche Medicale, Paris (FR)

(*) Notice: Subject to any disclaimer, the term of this patent is extended or adjusted under 35 U.S.C. 154(b) by 0 days.

(21) Appl. No.: 13/321,493

(22) PCT Filed: May 20, 2010

(86) PCT No.: PCT/EP2010/056953
§ 371 (c)(1),
(2), (4) Date: Nov. 18, 2011

(87) PCT Pub. No.: WO2010/133663
PCT Pub. Date: Nov. 25, 2010

(65) Prior Publication Data
US 2012/0064094 A1    Mar. 15, 2012

(30) Foreign Application Priority Data

May 20, 2009  (EP) .................................. 09305464
Oct. 21, 2009  (EP) .................................. 09305996

(51) Int. Cl.
*A01N 61/00* (2006.01)
*A61K 31/00* (2006.01)
*A61K 39/00* (2006.01)
*A61K 39/38* (2006.01)

(52) U.S. Cl.
USPC .......................................... 514/1; 424/184.1

(58) Field of Classification Search
None
See application file for complete search history.

(56) References Cited

U.S. PATENT DOCUMENTS

| | | | |
|---|---|---|---|
| 4,695,578 A | 9/1987 | Coates et al. | 514/397 |
| 4,789,673 A | 12/1988 | Donatsch et al. | 514/214.03 |
| 4,886,808 A | 12/1989 | King | 514/299 |
| 4,906,755 A | 3/1990 | Gittos | 546/94 |
| 4,939,136 A | 7/1990 | Haeck et al. | 514/183 |
| 5,202,333 A | 4/1993 | Berger et al. | 514/296 |
| 5,225,407 A | 7/1993 | Oakley et al. | 514/215 |
| 5,256,665 A | 10/1993 | Orjales-Venero et al. | 514/254.06 |
| 5,360,800 A | 11/1994 | Coates et al. | 514/215 |
| 5,677,326 A | 10/1997 | Tsuchiya et al. | 514/394 |
| 6,063,802 A * | 5/2000 | Winterborn | 514/397 |
| 6,770,655 B2 | 8/2004 | Zhang et al. | 514/292 |
| 2004/0204466 A1* | 10/2004 | Agarwal et al. | 514/381 |
| 2006/0074101 A1 | 4/2006 | Baroni et al. | 514/296 |
| 2007/0265329 A1 | 11/2007 | Devang et al. | 514/419 |
| 2010/0266607 A1* | 10/2010 | Fox | 424/157.1 |

FOREIGN PATENT DOCUMENTS

| | | |
|---|---|---|
| EP | 19156 | 11/1980 |
| EP | 94724 | 11/1983 |
| EP | 99789 | 2/1984 |
| EP | 200444 | 11/1986 |
| EP | 242973 | 10/1987 |
| EP | 247266 | 12/1987 |
| EP | 266730 | 5/1988 |
| EP | 302699 | 2/1989 |
| EP | 306323 | 3/1989 |
| EP | 307172 | 3/1989 |
| EP | 309423 | 3/1989 |
| EP | 313393 | 4/1989 |
| EP | 337547 | 10/1989 |
| EP | 339950 | 11/1989 |
| EP | 353983 | 2/1990 |
| EP | 356098 | 2/1990 |
| EP | 358903 | 3/1990 |
| EP | 381422 | 8/1990 |
| EP | 397364 | 11/1990 |
| EP | 397365 | 11/1990 |
| EP | 1 250 925 | 10/2002 |
| GB | 2100259 | 12/1982 |
| GB | 2125398 | 3/1984 |
| GB | 2153821 | 8/1985 |
| GB | 2160871 | 1/1986 |
| GB | 2202530 | 9/1988 |
| WO | WO 88/01866 | 3/1988 |

OTHER PUBLICATIONS

Brookes GB. Clinical Otolaryngology and Allied Sciences, 21(1):3-11, 1996.*
Lehrer JF. The International Tinnitus Journal, 10(1):84-86, Jan./Jun. 2004.*
Brookes, "The pharmacological treatment of Meniere's disease," *Clinical Otolaryngology and Allied Sciences*, 21(1):3-11, 1996.
Gil-Loyzaga et al., "Serotonergic innervation of the organ of Corti of the cat cochlea," *Nueroreport*, 8(16):3519-22, 1997.
Hain and Yacovino, "Pharmacologic Treatment of Persons with Dizziness", *Neurologic Clinics*, 23:831-853, 2005.
International Search Report, issued in International Patent Application No. PCT/EP2010/056953, mailed on Oct. 21, 2010.
Jellish et al., "Ondansetron versus droperidol or placebo when given prophylactically for the prevention of postoperative nausea and vomiting in patients undergoing middle ear procedures," *J Clinical Anesthesia*, 9(6):451-456, 1997.
Johnson and Heinemann, "Embryonic expression of the 5-HT3 receptor subunit, 5-HT3R-A, in the rat: an in situ hybridization study," *Mol. Cell Neurosci.*, 6(2):122-38, 1995.

(Continued)

*Primary Examiner* — Robert Landsman
(74) *Attorney, Agent, or Firm* — Fulbright & Jaworski LLP

(57) ABSTRACT

The invention relates to serotonin 5-HT3 receptor antagonists or inhibitors of serotonin 5-HT3 receptor gene expression for use in the treatment of a lesional vestibular disorder.

10 Claims, 8 Drawing Sheets

(56) References Cited

OTHER PUBLICATIONS

Figure 1:
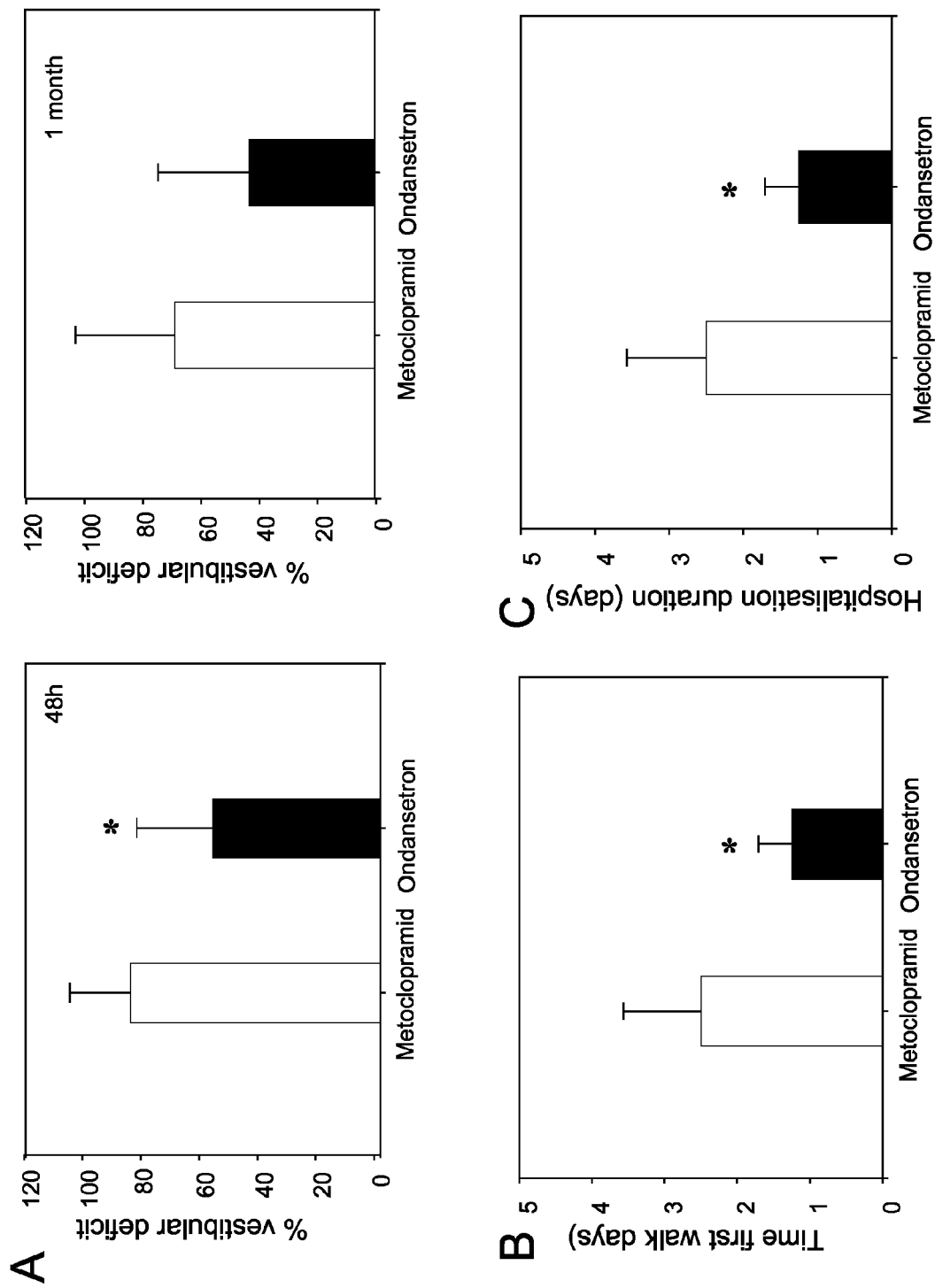

Kraut et al., "Anti-emetics for cancer chemotherapy-induced emesis: potential of alternative delivery systems," *Drugs*, 61(11):1553-1562, 2001.

Mandelcorn et al., "A preliminary study of the efficacy of ondansetron in the treatment of ataxia, poor balance and incoordination from brain injury," *Brain Injury*, 18(10):1025-1039, 2004.

Rice and Ebers, "Ondansetron for intractable vertigo complicating acute brainstem disorders," *The Lancet*, 345(8958):1182-1183, 1995.

Smith et al., "Zacopride, a potent 5-HT3 antagonist", J. Pharm. Pharmacol., 40: 301-302, 1988.

Tsukagoshi et al., Azasetron (Serotone®), 1999.

Tyers and Freeman, "Mechanism of the Anti-Emetic Activity of 5-HT3 Receptor Antagonists," *Oncology*, 49(4):263-268, 1992.

\* cited by examiner

C

D

METHODS OF TREATING LESIONAL VESTIBULAR DISORDERS BY ADMINISTERING SEROTONIN 5-HT3 RECEPTOR ANTAGONISTS

This application is a national phase application under 35 U.S.C. §371 of International Application No. PCT/EP2010/056953 filed 20 May 2010, which claims priority to European Application No. 09305464.1 filed 20 May 2009 and European Application No. 09305996.2 filed 21 Oct. 2009. The entire text of each of the above-referenced disclosures is specifically incorporated herein by reference without disclaimer.

FIELD OF THE INVENTION

The invention relates to serotonin 5-HT3 receptor antagonists or inhibitors of serotonin 5-HT3 receptor gene expression for use in the treatment or prevention of a lesional vestibular disorder.

BACKGROUND OF THE INVENTION

Introduction on Vestibular Disorders

Vestibular (inner ear) disorders can cause dizziness, vertigo, imbalance, hearing changes, nausea, fatigue, anxiety, difficulty concentrating, and other symptoms, with potentially devastating effects on a person's day-to-day functioning, ability to work, relationships with family and friends, and quality of life.

For example, vestibular neuritis is the first cause of hospitalisation for non neurological vertigos. Because its aetiology is largely unknown, epidemiological studies are variable depending on the source (its incidence is believed to be between 3.5 and 50 new cases for 100000 persons/per year). In the past, either an inflammation of the vestibular nerve or labyrinthine ischemia was proposed as a cause of vestibular neuritis. Currently, a viral cause is favoured. A reactivation of herpes simplex virus type 1 would explain the repetition of the vertigo crisis under such a situation.

Vestibular disorders may be also involved in the majority of the fall in the elderly and their prevention became a priority. The fall in the elderly represents indeed more than 1% of the total budget of the health insurance in France (INSEE 1990). It affects in France 30% of people above 65 and 50% above 80. The fall in the elderly is involved in ⅔ of the death caused by accident above 65, and multiplies by 4 the risk of death in the following year.

Aetiology of Vestibular Disorders

Although the aetiology of vestibular disorders is mostly unknown, it is widely accepted that vestibular disorders (also called vestibular deficits) constitute a vast family of conditions wherein the vestibule organ is associated. These disorders may be distinguished by their putative origins, one can thus identify (1) lesional vestibular disorders and (2) non lesional vestibular disorders.

1) Lesional vestibular disorders refer to vestibular disorders wherein lesions on inner ear cells and/or vestibular nerve are present or will appear during the disorder time course. In this case, the functionality of the vestibule is impaired as it can be observed using clinical functional tests (VOR, VNG). Lesional vestibular disorders include:

vestibular disorders wherein an infection inflames the inner ear and/or the vestibular nerve inducing reversible and/or irreversible damages. One example of conditions from this group is vestibular neuritis.

vestibular disorders wherein inner ear fluid levels are affected (abnormalities in the quantity, composition, and/or pressure of the endolymph), these disorders usually develop lesions during the disease time course. Examples of conditions from this group are Ménière's disease and secondary endolymphatic hydrops. They are currently associated with tinnitus and hearing loss.

Vestibular disorders induced by insults or lesions of the vestibular endorgans. Examples of said conditions are vertigo caused by local ischemia, excitotoxicity, trauma that affect temporal bones.

2) Non-lesional vestibular disorders refer to vestibular disorders supported by transient and often iterative vertigo crisis wherein no lesion on inner ear cells and/or vestibular nerve can be observed. In this case, the functionality of the vestibule evaluated between the vertigo crisis using functional tests (VOR, VNG) do not differ from healthy vestibule. Non-lesional vestibular disorders include:

vestibular disorders wherein debris had been collected within a part of the inner ear. This debris, called otoconia, is made up of small crystals of calcium carbonate and when they shift, they send false signals to the brain. Examples of said conditions are positional vertigos.

Iterative vestibular disorders of unknown origin without tinnitus or hearing loss.

Evaluation of the Vestibule Functional Loss

In human, morphofunctional alterations of the vestibular endorgans cannot be evaluated directly (excepted for large lesions that can be detected by IRM). Rather indirect assessment methods are currently used to evaluate the loss of functionality of the vestibule. These behaviour testing methods are generally conducted at ENT clinic/hospitals. Among them we can cite the vestibulonystagmography (VNG), assessment of the vestibuloocculomotor reflex (VOR) using caloric or rotational tests.

Treatments of Vestibular Deficits

Current treatments of vestibular deficits mainly focus on reducing the vertigo crisis using vestibuloplegic drugs, while limiting neurovegetative reactions by using anti emetic drugs. Corticosteroids and antiviral drugs are the only medication that tries to limit the spread of vestibular damages in the case of vestibular neuritis (that are assumed to be due to bacterial or virus infections). Their effect remains under debate regarding the lack of aetiology in most vestibular deficits. For example, recovery after vestibular neuritis is usually incomplete. In a study of 60 patients, horizontal semicircular canal paresis was found in about 90% one month after the onset of symptoms, and in 80% after six months; the caloric responses normalized in only 42%. On the basis of the incidence of this condition, a substantial and permanent unilateral dynamic deficit of the vestibulo ocular reflex, which cannot be compensated for by other mechanisms, develops in approximately 4000 person per year in the United States. This deficit leads to impaired vision and postural imbalance during walking and especially during head movement toward the affected ear.

Accordingly, there is a need for a protective or repair therapy that prevent, reduce or treat the incidence and/or severity of lesional vestibular disorders, said functional alteration of the inner ear cells and/or vestibular nerve being due to an inflammation, lesions or insults of diverse origins.

The inventors surprisingly found that serotonin 5-HT3 receptors antagonists such as ondansetron were able to prevent or treat vestibular lesions by protecting inner ear cells and vestibular nerve from damage or degeneration. Ondansetron is known from Jellish et al. (Journal of Clinical Anesthesia 2007, 9:451-456) for reduction of postoperative nausea or vomiting after chirurgical treatment of the middle ear. Ondansetron is also known from Rice et al. (The Lancet 1995, 345:1182-1183) for treating symptoms such as vertigo, nausea and vomiting in brainstem disorders such as multiple sclerosis. Finally, ondansetron is also known from US2007265329 for preventing nausea and vomiting induced by chemotherapy. The anti-emetic properties of ondansetron has been reported to be mediated by an antagonization of the 5-HT3 serotonin receptors located in the vomiting centre (brain stem lateral reticular formation) that receives vestibular, somatic, visceral and limbic afferents (Tyers M B, Freeman A J. Oncology, 1992, 49:263-268). This pharmacological action prevents the vomiting reflex usually mediated by serotonin.

While Ondansetron was used for treating or preventing emetic symptoms associated with vertigo, the inventors found that it is also capable of preventing and/or treating direct insults or lesions within vestibular organs.

SUMMARY OF THE INVENTION

The invention relates to serotonin 5-HT3 receptor antagonists or inhibitors of serotonin 5-HT3 receptor gene expression for the treatment of a lesional vestibular disorder.

DETAILED DESCRIPTION OF THE INVENTION

A recent clinical investigation carried out by the inventors demonstrated a suitable restorative effect of a serotonin 5-HT3 receptor antagonist (i.e. 1,2,3,9-tetrahydro-9-methyl-3-[(2-methyl-1H-imidazol-1-yl)methyl]-4H-carbazol-4-one, also known as ondansetron) on the vestibular impairments accompanying vestibular neuritis. This serotonin 5-HT3 receptor antagonist efficiently reduces the functional alteration of the vestibular endorgans and subsequently the vestibular deficit encountered under such inner ear pathology. This result is outstanding since it constitutes the first demonstration that a pharmacological therapy focused on the protection and/or the restoration of the vestibular functionality, may bring concrete solution to rescue vestibular functionality following lesional vestibular impairments. It also offers a unique opportunity to develop the first curative therapy against lesional vestibular deficits.

In addition, the inventors made for the first time the observation that serotonin 5-HT3 receptor proteins are expressed in several parts of the vestibule.

Therefore, the present invention provides methods and compositions (such as pharmaceutical compositions) for use in the treatment of lesional vestibular disorder.

As used herein, the terms "treating", "treatment", and "therapy" as used herein refer to curative therapy. Accordingly the aim of the invention is to provide a permanent ending of the vestibular disorders or an amelioration of the subject's condition by restoring the functionality or part of the functionality of the vestibular endorgans and therefore restoring the vestibular functionality. The invention does not provide a method for controlling the undesirable symptoms associated with vestibular deficit such as emesis and nausea but provides a method for curing the vestibular deficit. The invention also aims at preventing any lesion to appear or preventing lesion already present to increase.

The present invention provides methods and compositions (such as pharmaceutical compositions) for use in a method for protecting/restoring the vestibular neuronal network and accordingly for protecting/restoring the vestibular functionality in a subject affected with a lesional vestibular disorder.

As used herein, the term "lesional vestibular disorder or deficit" refers to vestibular disorders wherein lesions on inner ear cells and/or vestibular nerve are present or will appear during the disorder time course. In this case, the functionality of the vestibule is impaired. Lesional vestibular disorders include:

vestibular disorders wherein an infection inflames the inner ear and/or the vestibular nerve inducing reversible and/or irreversible damages. One example of conditions from this group is vestibular neuritis.

vestibular disorders wherein inner ear fluid levels are affected (abnormalities in the quantity, composition, and/or pressure of the endolymph), these disorders usually develop lesions during the disease time course. Examples of conditions from this group are Ménière's disease and secondary endolymphatic hydrops.

Vestibular disorders induced by insults or lesions of the vestibular endorgans. Examples of said conditions are vertigo causes by local ischemia, excitotoxicity, trauma that affect temporal bones.

Examples of lesional vestibular disorder that are contemplated by the invention include but are not limited to vestibular neuritis, viral neuronitis, labyrinthitis, viral endo lymphatic labyrinthitis, drug-induced ototoxicity, Ménière's disease, endo lymphatic hydrops, head trauma with lesional vestibular deficits, labyrinthine haemorrhage, chronic or acute labyrinthine infection, serous labyrinthine, barotraumatism, autoimmune inner ear disease, presbyvestibulia, toxic vestibular impairments.

According to the invention, lesional vestibular disorders may be identified using IRM for large lesions or by indirect assessment methods allowing the evaluation of the loss of functionality of the vestibule. These methods are generally conducted at ENT clinic/hospitals and include the vestibulonystagmography (VNG), and assessment of the vestibulooculomotor reflex (VOR) using caloric or rotational tests. The function of the vestibulo-ocular reflex (VOR) is to stabilize the visual image on the retina during displacement. Measurement of this VOR provides convenient method to investigate the functionality of the vestibular system. Basically, the paradigm in based on monitoring eyes movements by infrared light projection technique (Fetoni et al. 2003, Hearing Research 2003, 182:56-64). Patients are sinusoidally oscillated in the dark around their vertical and longitudinal axes in order to evoke horizontal and vertical eye responses. Any functional impairment of the vestibule is associated with alterations in the gain of the evoked VNG. Besides VOR and VNG, posturography methods are used to detect postural deviations of the body that are also related to impairments of the vestibule. Morphofunctional investigations such as functional imaging (IRM or CAT (computerized axial tomography) and derivates) can be used to detect profound lesions within the vestibular endorgans. Specifically adapted VNG, VOR and postural testings are used in animal models of vestibular deficits to evaluate the amplitude of the insults or lesions in the vestibule. Histological studies are also possible using conventional light or electron microscopy on fixed tissue (vestibular ganglia and vestibular endorgans). Such investigations are mostly done in rodents.

As used herein, the term "subject" denotes a mammal, such as a rodent, a feline, a canine, and a primate. Preferably, a subject according to the invention is a human.

According to an aspect, the invention relates to a serotonin 5-HT3 receptor antagonist for use in the treatment of a lesional vestibular disorder.

According to another aspect, the invention relates to a serotonin 5-HT3 receptor antagonist for use in a method for restoring vestibular functionality in a subject affected with a lesional vestibular disorder. Said restoration may be evaluated using the VNG or assessment of the VOR as mentioned here above.

As used herein, the term "serotonin 5-HT3 receptor" has its general meaning in the art and refers to 5-hydroxytryptamine (serotonin) receptor subtype 3. The term may include naturally occurring serotonin 5-HT3 receptor and variants and modified forms thereof. The serotonin 5-HT3 receptor can be from any source, but typically is a mammalian (e.g., human and non-human primate) serotonin 5-HT3 receptor, particularly a human serotonin 5-HT3 receptor.

As used herein, the term "serotonin 5-HT3 receptor antagonist" includes any chemical entity that, upon administration to a patient, results in inhibition or down-regulation of a biological activity associated with activation of the serotonin 5-HT3 receptor in the patient, including any of the downstream biological effects otherwise resulting from the binding to serotonin 5-HT3 receptor of its natural ligand (i.e. serotonin). Such serotonin 5-HT3 receptor antagonists include any agent that can block serotonin 5-HT3 receptor activation or any of the downstream biological effects of serotonin 5-HT3 receptor activation. For example, such a serotonin 5-HT3 receptor antagonist can act by occupying the ligand binding site or a portion thereof of the serotonin 5-HT3 receptor, thereby making the receptor inaccessible to its natural ligand so that its normal biological activity is prevented or reduced. The antagonistic activity of compounds towards the serotonin 5-HT3 receptors may be determined by using various methods well known in the art. For example 5-HT3 antagonistic activity may be evaluated in a radioligand binding assay and in the 5-HT-induced von Bezold-Jarisch reflex in the rat such as described by Turconi M. et al. (1990) that is hereby incorporated by reference.

In one embodiment, the serotonin 5-HT3 receptor antagonist may be a small organic molecule.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

Exemplary serotonin 5-HT3 antagonists that are contemplated by the invention include but are not limited to the small organic molecules described in U.S. Pat. Nos. 4,695,578; 4,906,755; 4,886,808; 5,677,326; 5,202,333; 5,225,407; 5,360,800 6,770,655; UK patent application Nos. 2100259, 2125398, 2153821, 2160871 and 2202530; published European patent applications Nos. 94724, 99789, 200444, 242973, 247266, 266730, 302699, 306323, 307172, 309423, 313393, 337547, 339950, 353983, 356098, 358903, 381422, 397364 and 397365; and PCT Patent Application No. 88/01866 that are hereby incorporated by reference.

According to a particular embodiment, the serotonin 5-HT3 receptor antagonist for use according to the invention may be a compound of formula (I):

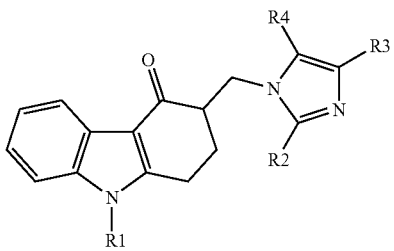

wherein R1 represents a $C_{3-7}$ cycloalkyl-$(C_{1-4})$alkyl group or a $C_{3-10}$ alkynyl group; and one of the groups represented by R2, R3 and R4 is a hydrogen atom or a $C_{1-6}$ alkyl, $C_{3-7}$ cycloalkyl, $C_{2-6}$ alkenyl or phenyl-$(C_{1-3})$alkyl group and each of the other two groups, which may be the same or different, represents a hydrogen atom or a $C_{1-6}$ alkyl group; and physiologically acceptable salts, free acid forms, free base forms and solvates (e.g. hydrates) thereof.

Compounds of formula (I) were described in European Patent no. 19156 and in U.S. Pat. No. 4,695,578 that are hereby incorporated by reference into the present disclosure.

When the group R1 in general formula (I) represents a $C_{3-7}$ cycloalkyl-$(C_{1-4})$ alkyl group, the $C_{3-7}$ cycloalkyl moiety may be, for example, a cyclopropyl, cyclobutyl, cyclopentyl, cyclohexyl or cycloheptyl group; and the $C_{1-4}$ alkyl portion may be a methyl, ethyl, propyl, prop-2-yl or butyl group. The group R1 may therefore represent, e.g. a cyclopropylmethyl, cyclooentylpropyl or a cycloheptylmethyl group. When the cycloalkyl ring contains 5, 6 or 7 carbon atoms it may optionally contain one or two double bonds. Examples of such groups include cyclohexenyl and cyclohexadienyl groups.

When R1 represents a $C_{3-10}$ alkynyl group, this may be, for example, a 2-propynyl or 2-octynyl group. It will be understood that when R represents a $C_{3-10}$ alkynyl group, the triple bond may not be adjacent to the nitrogen atom.

Referring to the groups represented by R2, R3 and R4 in general formula (I), an alkyl group may be a straight chain or branched chain alkyl group, for example, a methyl, ethyl, propyl, or prop-2-yl, group; an alkenyl group may be, for example, a propenyl group; a phenyl-$(C_{1-3})$ alkyl group may be, for example, a benzyl, phenethyl or 3-phenylpropyl group; and a cycloalkyl group may be, for example, a cyclopentyl, cyclohexyl or cycloheptyl group.

It will be appreciated that the carbon atom at the 3-position of the tetrahydrocarbazolone ring is asymmetric and may exist in the R-or S-configuration. Furthermore, it will be appreciated that depending upon the nature of the groups R1, R2, R3 and R4, centres of isomerism may occur elsewhere in the molecule. The present invention encompasses all the individual isomeric forms of the compounds of formula (I) and all mixtures thereof.

In a preferred embodiment, the invention encompasses the use of the optically pure R(+) isomers of compounds of formula (I).

Suitable physiologically acceptable salts of the compounds of general formula (I) include acid addition salts formed with organic or inorganic acids for example, hydrochlorides, hydrobromides, sulphates, phosphates, citrates, fumarates and maleates. The solvates may, for example, be hydrates.

A preferred class of compounds represented by the general formula (I) is that wherein one of the groups represented by R2, R3 and R4 represents a $C_{1-3}$ alkyl or $C_{3-6}$ alkenyl group and each of the other two groups, which may be the same or different, represents a hydrogen atom or a $C_{1-3}$ alkyl group.

When R2 represents a hydrogen atom, R3 and/or R4 preferably represents a $C_{1-3}$ alkyl group. When R2 represents a $C_{1-3}$ alkyl group R3 and R4 both preferably represent hydrogen atoms.

Preferred compounds of formula (I) may be 1,2,3,9-tetrahydro-3-[(2-methyl-1H-imidazol-1-yl)methyl]-9-(prop-2-enyl)-4H-carbazol-4-one; 9-cyclopentyl-1,2,3,9-tetrahydro-3-[(2-methyl-1H-imidazol-1-yl)methyl]-4H-carbazol-4-one; and 1,2,3,9-tetrahydro-3-[2-methyl-1H-imidazol-1-yl)methyl]-9-(prop-2-yl)-4H-carbazol-4-one and their physiologically acceptable salts and solvates.

A particularly suitable serotonin 5-HT3 antagonist for use according to the invention is Ondansetron®, that is the approved name for 1,2,3,9-tetrahydro-9-methyl-3-[(2-methyl-1H-imidazol-1-yl)methyl]-4H-carbazol-4-one which may be represented by the formula:

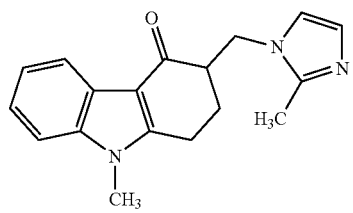 [SMILES: Cc1nccn1CC1CCc2c(c3ccccc3n2C)C1=O]

and the physiologically acceptable salts, free acid forms, free base forms and solvates (e.g. hydrates) thereof.

Other particularly suitable serotonin 5-HT3 antagonists for use according to the invention may be selected from the group consisting of palonosetron, tropisetron, lerisetron, alosetron, granisetron, dolasetron, bernesetron, ramosetron, azasetron, itasetron, zacopride, and cilansetron.

Palonosetron is (3aS)-2-[(S)-1-azabicyclo[2.2.2]oct-3-yl]-2,3,3a,4,5,6-hexahydro-1-oxo-1Hbenz[de]isoquinoline and is described in U.S. Pat. No. 5,202,333.

Tropisetron, is (+−) 1H-Indole-3-carboxilic acid (3-endo)-8-methyl-8-azabicyclo[3.2.1]oct-3-yl-ester and is described in U.S. Pat. No. 4,789,673.

Lerisetron is (1-(phenylmethyl)-2-(1-piperazinyl)-1H-benzimidazole) and is described in U.S. Pat. No. 5,256,665.

Alosetron is 2,3,4,5-tetrahydro-5-methyl-2-[(5-methyl-1H-imidazol-4-yl)methyl]-1H-pyrido[4,3-b]indol-1-one and is described in U.S. Pat. No. 5,360,800.

Granisetron is endo-N-(9-methyl-9-azabicyclo[3.3.1]non-3-yl)-1-methyl-1H-indazole-3-carboxamide and is described in U.S. Pat. No. 4,886,808.

Dolasetron is (2[alpha],6[alpha],8[alpha],9[alpha][beta])-octahydro-3-oxo-2,6-methano-2H-quinolizin-8-yl-1H-indole-3-carboxylate, and is described in U.S. Pat. No. 4,906,755.

Ramosetron is (−)-(R)-5-[(1-methyl-1H-indol-3-yl) carbonyl]-4,5,6,7-tetrahydro -1H-and is described in European Patent Application No. 381422 A1.

Azasetron is N-1-Azabicyclo[2.2.2]oct-3-yl-6-chloro-3,4-dihydro-4-methyl-3-oxo-2H-1,4-benzoxazine-8-carboxamide hydrochloride.

Itasetron is (3-alpha-tropanyl)1H-benzimidazolone-3-carboxamide hydrochloride.

Zacoprid is 4-amino-N-(1-azabicyclo[2.2.2]oct-3-yl)-5-chloro-2-methoxybenzamide and is described in European Patent Application No. 099789 A1.

Cilansetron is R-(−)5,6,9,10-tetrahydro-10-[(2-methyl-imidazol-1-yl)methyl]-4H-pyrido[3.2.1-jk]carbazol-11 (8H)-one, and is described in U.S. Pat. No. 4,939,136.

In another embodiment the serotonin 5-HT3 receptor antagonist for use according to the invention may consist in an antibody (the term including antibody fragment) that can block serotonin 5-HT3 receptor activation.

In particular, the serotonin 5-HT3 receptor antagonist may consist in an antibody directed against the serotonin 5-HT3 receptor or a ligand of the serotonin 5-HT3 receptor, in such a way that said antibody impairs the binding of a ligand to said receptor.

Antibodies directed against the serotonin 5-HT3 receptor can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against serotonin 5-HT3 receptor or ligands of serotonin 5-HT3 receptors can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-5-HT3, or anti-5-HT3 ligands single chain antibodies. serotonin 5-HT3 receptor antagonists useful in practicing the present invention also include anti-5-HT3, or anti-5-HT3 ligands antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to serotonin 5-HT3 receptor.

Humanized anti-serotonin 5-HT3 receptor or anti-5-HT3 ligands antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then after raising antibodies directed against the serotonin 5-HT3 receptor as above described, the skilled man in the art can easily select those blocking serotonin 5-HT3 receptor activation.

In another embodiment the serotonin 5-HT3 receptor antagonist for use according to the invention is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Then after raising aptamers directed against the serotonin 5-HT3 receptor as above described, the skilled man in the art can easily select those blocking serotonin 5-HT3 receptor activation.

Serotonin 5-HT3 receptor antagonists for use according to the invention can be further identified by screening methods described in the state of the art. The screening methods of the invention can be carried out according to known methods. The screening method may measure the binding of a candidate compound to the 5-HT3 receptor, or to cells or membranes bearing the 5-HT3 receptor, or a fusion protein thereof by means of a label directly or indirectly associated with the candidate compound. Alternatively, a screening method may involve measuring or, qualitatively or quantitatively, detecting the competition of binding of a candidate compound to the 5-HT3 receptor with a labelled competitor (e.g., antagonist or agonist). Further, screening methods may test whether the candidate compound results in a signal generated by an antagonist of the receptor, using detection systems appropriate to cells bearing the receptor. Antagonists can be assayed in the presence of a known agonist (e.g. serotonin) and an effect on activation by the agonist by the presence of the candidate compound is observed. Competitive binding using known agonist such as serotonin is also suitable. The antagonistic activity of compounds towards the serotonin 5-HT3 receptors may be determined by using various methods well known in the art. For example 5-HT3 antagonistic activity may be evaluated in a radio ligand binding assay and in the 5-HT-induced von Bezold-Jarisch reflex in the rat such as described by Turconi M. et al. (1990).

Another aspect of the invention relates to an inhibitor of serotonin 5-HT3 receptor gene expression for use in the treatment of a lesional vestibular disorder.

According to another aspect, the invention relates to an inhibitor of serotonin 5-HT3 receptor gene expression for use in a method for restoring vestibular function in a subject affected with a lesional vestibular disorder.

An "inhibitor of gene expression" refers to a natural or synthetic compound that has a biological effect to inhibit or significantly reduce the expression of a gene. Consequently an "inhibitor of serotonin 5-HT3 receptor gene expression" refers to a natural or synthetic compound that has a biological effect to inhibit or significantly reduce the expression of the gene encoding for the serotonin 5-HT3 receptor.

Inhibitors of serotonin 5-HT3 receptor gene expression for use in the present invention may be based on anti-sense oligonucleotide constructs. Anti-sense oligonucleotides, including anti-sense RNA molecules and anti-sense DNA molecules, would act to directly block the translation of serotonin 5-HT3 receptor mRNA by binding thereto and thus preventing protein translation or increasing mRNA degradation, thus decreasing the level of serotonin 5-HT3 receptors, and thus activity, in a cell. For example, antisense oligonucleotides of at least about 15 bases and complementary to unique regions of the mRNA transcript sequence encoding serotonin 5-HT3 receptor can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of serotonin 5-HT3 receptor gene expression for use in the present invention. Serotonin 5-HT3 receptor gene expression can be reduced by contacting a subject or cell with a small double stranded RNA (dsRNA), or a vector or construct causing the production of a small double stranded RNA, such that serotonin 5-HT3 receptor gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of serotonin 5-HT3 receptor gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of serotonin 5-HT3 receptor mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of serotonin 5-HT3 receptor gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing serotonin 5-HT3 receptor. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adeno-viruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Another object of the invention relates to a method for the treatment of a lesional vestibular disorder comprising administering a subject in need thereof with a serotonin 5-HT3 receptor antagonist or an inhibitor of serotonin 5-HT3 receptor gene expression.

Another object of the invention relates to a method for restoring vestibular functionality in a subject affected with a lesional vestibular disorder comprising administering a subject in need thereof with a serotonin 5-HT3 receptor antagonist or an inhibitor of serotonin 5-HT3 receptor gene expression.

Serotonin 5-HT3 receptor antagonists or inhibitors of serotonin 5-HT3 receptor gene expression may be administered in the form of a pharmaceutical composition, as defined below.

Preferably, said antagonist or inhibitor is administered in a therapeutically effective amount.

By a "therapeutically effective amount" is meant a sufficient amount of the serotonin 5-HT3 receptor antagonist or inhibitor of serotonin 5-HT3 receptor gene expression to treat or prevent vestibular deficits at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. The composition of the invention may comprise the serotonin 5-HT3 receptor antagonist in a range of 0.01 mg to 500 mg, preferably from 0.05 mg to 250 mg, from 0.1 mg to 100 mg, from 0.5 mg to 50 mg, from 1 mg to 25 mg, from 2.5 mg to 15 mg, from 5 mg to 15 mg, from 8 mg to 12 mg. An effective amount of the drug is ordinarily supplied at a dosage level from 0.0002 mg/kg to about 20 mg/kg of body weight per day, especially from about 0.001 mg/kg to 7 mg/kg of body weight per day.

The serotonin 5-HT3 receptor antagonist or inhibitor of serotonin 5-HT3 receptor gene expression may be combined with pharmaceutically acceptable excipients, and optionally sustained-release matrices, such as biodegradable polymers, to form therapeutic compositions.

The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The serotonin 5-HT3 receptor antagonist or inhibitor of serotonin 5-HT3 receptor gene expression of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and anti-fungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active ingredients in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The serotonin 5-HT3 receptor antagonist or inhibitor of serotonin 5-HT3 receptor gene expression of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

In a particular embodiment, the serotonin 5-HT3 receptor antagonist or inhibitor of serotonin 5-HT3 receptor gene expression is administered directly in the inner ear through the tympanic membrane. This administration mode may be preferred for introducing a direct and long term effect on the vestibule. Accordingly in a preferred embodiment, the serotonin 5-HT3 receptor antagonist or inhibitor of serotonin 5-HT3 receptor gene expression is administered in a gel formulation to allow a long term release of said antagonist or inhibitor in the inner ear.

In another embodiment of the invention, the composition of the invention is formulated for nasal administration. Several advantages are offered by nasal administration:
dose of the active compound can be reduced as it is rapidly absorbed by the mucosa and the bioavailability is high
onset of therapeutic action is fast
hepatic first pass metabolism is avoided
a metabolism in gastrointestinal tract can be avoided
patient compliance is improved.

Nasal route of administration of serotonin 5-HT3 receptor antagonist provides rapid delivery of active drug to the blood through the highly permeable nasal mucosa and avoid the hepatic first pass effect. The advantage of this route of administration is that it is not aggressive and allows self administration. Another advantage is the rapid onset of action after inhalation and the higher bioavailability compared to oral administration which lead to anticipate improved efficacy. This route is also very convenient to treat patients received at the emergency room. They are usually stressed by the vertigos and nasal route is easier to administer than IV and is more relevant than oral administration especially when patients suffer from nausea or are vomiting. Another advantage consists in avoiding additional oral (tablets/capsules) intake, which is interesting in elderly patients, who are receiving multi medications for other diseases and would take advantage of the nasal route. In patient with liver failure, the nasal route of ondansetron should be recommended and preferred to the oral or IV route. The risk of accidental overdose is limited with the nasal formulation.

Thus, one object of the present invention is a serotonin 5-HT3 receptor antagonist for use in the treatment of a lesional vestibular disorder as described here above, wherein the composition comprising the serotonin 5-HT3 receptor antagonist is in a form suitable for nasal administration. Another object of the invention is a device for nasal administration of a serotonin 5-HT3 receptor antagonist for use in the treatment of a lesional vestibular disorder.

Said administration route allows a better bioavailability of the active agent compared to other administration route and is of interest for treating subjects that may suffer from vomiting.

Suitable forms for administering the serotonin 5-HT3 receptor antagonist into the nasal cavity are drops or sprays. Spray devices can be single (unit) dose or multiple dose systems, for example comprising a bottle, pump and actuator. Spray devices generally dispense between 0.04 and 0.25 ml in a single actuation. Typical nasal dosing regimens range from a single spray into one nostril to up to two sprays into each nostril.

The composition comprising the serotonin 5-HT3 receptor antagonist may further comprise carriers or bases, pH adjustors, preservatives, stabilizers, flavors and absorbefacients.

Examples of carriers or bases include, but are not limited to, water, hydroxypropyl cellulose, alginic acid, chitosan or gamma polyglutamate. Examples of pH adjustors include, but are not limited to, dibasic sodium phosphate, citric acid or sodium citrate. Examples of preservatives include, but are not limited to, sodium chloride or potassium sorbate. Examples of flavors include, but are not limited to, D-sorbitol, glycyrrhizia, saccharin, or stevia. Examples of absorbefacients include, but are not limited to, bile acid.

The composition of the invention for nasal administration may comprise the serotonin 5-HT3 receptor antagonist in a range of 0.01 mg to 500 mg, preferably from 0.05 mg to 250 mg, from 0.1 mg to 100 mg, from 0.5 mg to 50 mg, from 1 mg to 25 mg, from 2.5 mg to 15 mg, from 5 mg to 15 mg, from 8 mg to 12 mg.

One example of a composition according to the invention for nasal administration is a water-based composition comprising ondansetron base, sodium chloride, potassium sorbate, and citrate.

The invention will be further illustrated by the following figures and examples. However, these examples and figures should not be interpreted in any way as limiting the scope of the present invention.

FIGURES

FIGS. 1A-1C: Illustration of the clinical effects of ondansetron versus Metoclopramid in a sample of 20 patients. Illustration of the clinical effects of five days treatment with ondansetron (8 mg/j, n=10) versus Metoclopramid (30 mg/j, n=10) in a sample of 20 patients. Both molecules were administered together with vestibuloplegics, corticosteroids and antiviral drugs, in patients presenting a suspicion of vestibular neuritis. Vestibulonystagmography was used 48h and 1 month after the treatment (5 days duration) to assess the evolution of the vestibular deficit (A). On the early caloric tests, the vestibular deficit was less pronounced (56, 53% versus 84,38%, p=0,03) in patients treated with ondansetron versus metoclopramid. After one month, the difference was not significative anymore on our sample (43,0% ondansetron versus 63,4% metoclopramid, p=0,07). The time of first walk (B) and hospitalisation duration (C) were also significantly reduced in patients administrated with ondansetron.

FIGS. 2A-2D: Expression of 5HT-3 receptors in the mammal vestibule. (A) immunocytological detection of 5HT-3A receptors in the Scarpa's ganglion (A) and vestibular sensory epithelia (B-D). In A, noted that Schwann cell and endothelial cells were not labeled. In B-D, noted that 5HT-3A receptors were specifically expressed by transitional cells (large arrows) surrounding the sensory epithelia and in few nerve fibers (arrowheads).

FIGS. 3A-3B: Behavioral evaluation of the ondansetron effect on excitotoxically (kainate)-induced vestibular deficits. (A) protocol used to induce unilateral lesional vestibular deficit. Ondansetron was injected intraperitoneally (ip) at 4 mg/kg. 1h after KA injection, vestibular behavior of the animals was tested followed by ondansetron injection in the treatment group. Control animals did not receive an ondansetron injection. Subsequently, the animals were tested at 2 h, 6 h, 24 h and 48 h after KA injection. (B) Behavioral expression of the kainiteinduced vestibular deficit. Following transtympanic kainic acid injection, rats exhibit strong excitotoxically induced vestibular deficits which gradually decrease in 48 hours. This time course of decreased vestibular deficits is altered when animals are treated with ondansetron, with significantly reduced vestibular deficits at 24 hours (*p=0,022; Mann Whitney test; n>8). Subsequently, both treated and untreated animals recover to similar vestibular deficit levels due to endogenous compensatory mechanisms.

FIGS. 4A-4D: Histological evaluation of the excitotoxically (kainate)-induced vestibular lesions. KA induces a large exocytotic lesion of the vestibular afferents in the sensory epithelia 2 hrs after its transtympanic injection (A), in opposite to the contra-lateral not-lesioned ear (C). Large swelled synaptic endings were observed along hair cells instead of the typical calycealtype I and bouton-type II nerve endings. 24 hrs after the lesion, newly calyceal and boutons endings were observed with (B) and without (D) ondansetron.

Figure 5:
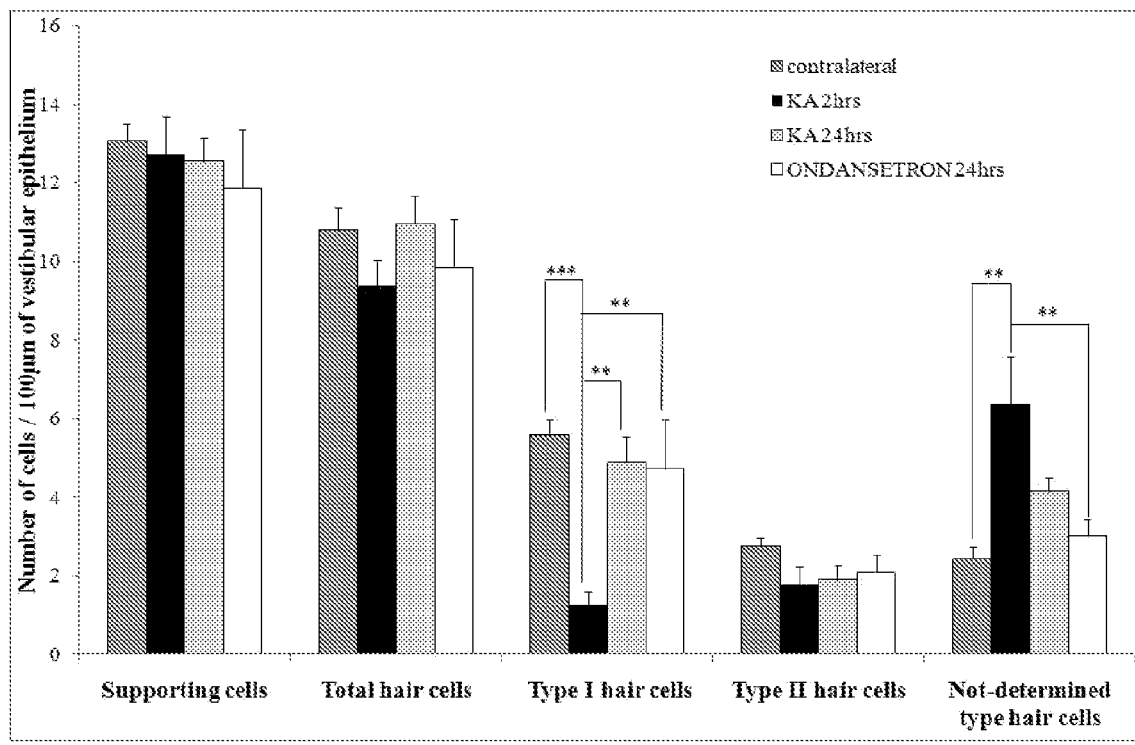

FIG. 5: Morphometric analysis of the excitotoxically (kainate)-induced vestibular lesions. No loss of hair or supporting cells was induced by the transtympanic injection of KA. Conversely, the number of identified type I hair cells with their surrounding calyx was largely and significantly reduced by KA (P<0.001), confirmed by the increased number of not-determined hair cell cells (P<0.01). When counted 24 hrs after the exocytotic injury, the number of type I hair cells newly identified was significantly increased (p<0.01), but the number of not-determined hair cells not significantly reduced. For Ondansetron treatment, we observed a significantly increased number of type I hair cells 24 hours after the KA lesion (p<0.01). The number of not-determined hair cells was significantly reduced by the ondansetron treatment (P<0.01).

FIGS. 6A-6E: Behavioral evaluation of the ondansetron effect on bilateral (nitrile)- induced vestibular deficits. (A) protocol used to induce bilateral lesional vestibular deficit. (BE) Time course of vestibular deficits expression in presence or absence of ondansetron treatment. The increasing vestibular deficits is not significantly altered when animals received ondansetron simultaneously (B), 24 h (C) or 48 h (D) after IDPN injection. Conversely, significant modification of the time course of increasing vestibular deficit occured (p=0,029) when ondansetron is injected 24 and 48 hours (E) after vestibular deficit induction.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1

Reduction of Vestibular Deficit Following Acute Vestibular Neuritis by Ondansetron (FIG. 1)

Methods: A clinical study conducted by the inventors at the Centre Hospitalier Universitaire (CHU) of Montpellier was carried out. Random clinical tests were performed on 20 patients. Patients were selected on the suspicion of vestibular neuritis started for less than 24 h before the hospitalization. The patients were all administered with methylprednisolone and valacyclovir, and either a 5 days treatment with Metoclopramide (30 mg/d, n=10) or with Ondansetron (8 mg/d, n=10). The functional evaluation was based on a early VNG (vestibulonystagmography) test (realized 24 to 48 hours after the beginning of the vestibular deficit) and a VNG at 1 month. The hospitalization duration and the date of the first walk were also recorded.

Results: Regarding the early VNG, the vestibular deficit was less pronounced in patients administered with ondansetron (56.53% versus 84.38%, p=0.03). At 1 month, the vestibular deficit did not differed in the two groups of patients (43% O versus 63.4% M, p=0.07). The hospitalization duration was significantly reduced in the ondansetron group (2.88 versus 4.5 days, p=0.03). The time of first walk was also significantly shorter (1.25 versus 2.25 days, p=0.001).

This clinical study demonstrated that ondansetron displays significant effect in reducing the vestibular deficit following acute vestibular neuritis in human (FIG. 1A). Clinical investigations of the vestibular function using caloric testing suggest a direct protective or restorative effect on the peripheral vestibular endorgans. That pharmacological effect does not interfere with the long term central compensation. Its consequence is a significant relieve of the dizziness and a reduction of the hospitalisation duration (FIG. 1B-C). These clinical observations indicate that ondansetron and its derivatives may be useful in the maintenance and restoration of innervation within the vestibule.

Example 2

The Cellular Targets of Serotonin 5-HT3 Antagonists are Expressed in the Vestibular Endorgans The putative direct effect of serotonin 5-HT3 receptor antagonists on the vestibule is supported by previous report that the serotonin receptors are expressed in the inner ear and specifically in the vestibular endorgans (Johnson and Heinemann, 1995; Gil-Loyzaga et al., 1997), and recent histological experiment from inventors that the 5-HT3 receptors proteins are present in the vestibular epithelia.

Methods:

Immunohistochemical localization of pharmacological targets in the vestibule.

We anesthetized female adult rats (Wistar; 200-220 g, n=2) with pentobarbital (0.4%). Animals were perfused transcardially with heparin PBS (0.01M) followed by a fixative solution (4% paraformaldehyde, 1% picric acid, 5% sucrose) and samples post-fixed. We embedded vestibular ganglia and epithelia in 4% agarose, and cut 40 µm thick sections. Pre-incubation in blocking solution (0.5% fish gelatin, 0.5% Triton X-100 and 1% BSA in PBS) prevented non-specific binding. Samples were then incubated with primary antibodies: rabbit polyclonal antibodies anti-5HT-3A receptors (1:200; AB5657; Millipore, Billerica, Mass.). For control, we omitted the investigated primary antibody. Secondary antibodies revealed specific labeling with Alexa 594-conjugated donkey anti-rabbit sera (1:200, Molecular Probes, Eugene, Oreg.). Zeiss 5 live duo laser scanning confocal microscope (RIO imaging, Montpellier, France) allowed the observation of samples mounted on slides.

Figure 2:
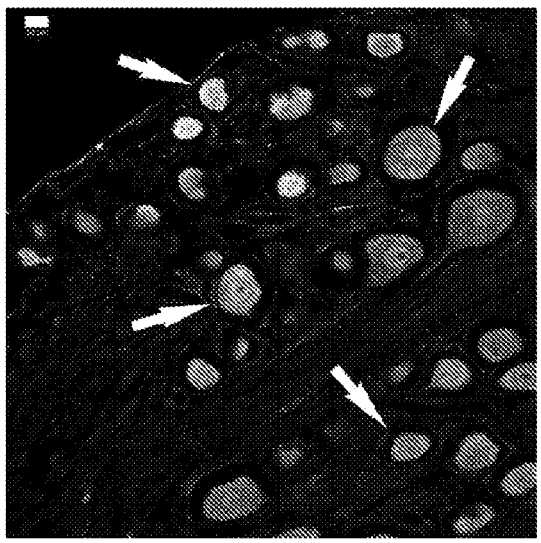
Figure 2:
Figure 2:
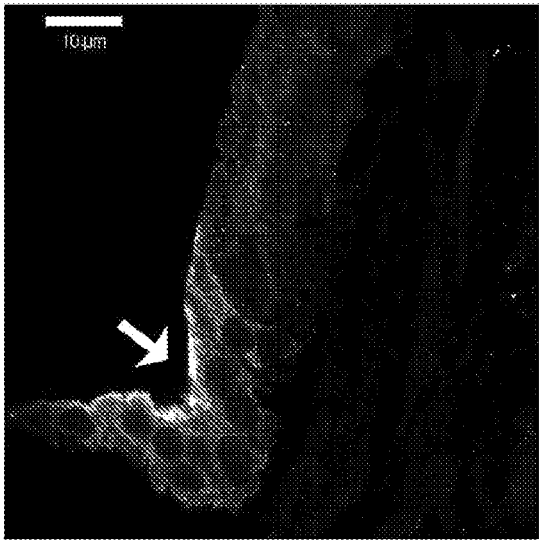
Figure 2:
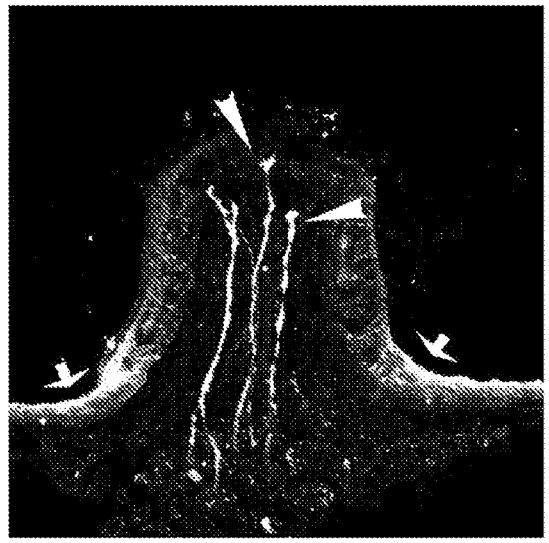

Results:

As shown in FIG. 2, 5HT-3 receptors are expressed in the Scarpa's ganglion (FIG. 2A). All primary vestibular neurons (arrows) were stained for 5HT-3A receptors, the large as well as small sized soma were immunofluorescent. Schwann cell and endothelial cells were not labeled. In vestibular sensory epithelia (FIG. 2B-D), 5HT-3A receptors were specifically expressed by transitional cells (large arrows) surrounding the sensory epithelia and in few nerve fibers (arrowheads). Co-staining with neurofilaments and calcium binding proteins (data not shown) strongly suggests a very restricted expression to distinct efferent fibers.

Example 3

Validation of the Restorative Effect of Ondansetron

Present example intends to validate on animal models of vestibular deficits the restorative effect on the vestibular endorgans of a serotonin 5-HT3 receptor antagonist that may selected from the group consisting of ondansetron, granisetron, tropisetron, or palonosetron observed in human. It also intends determining the biological process (protection/repair) involved in that process. This is assessed by comparing the time courses of histological damages and vestibular deficits in both models of unilateral and bilateral vestibular deficits under application of said serotonin 5-HT3 receptor antagonist. Combination of the two distinct animal models of vestibular deficits allows determining the benefice of using said serotonin 5-HT3 antagonist in conditions of unilateral or bilateral vestibular deficits. To our knowledge, they are the first paradigms focused on the mammal vestibular system. Determination of the biological process involved in the restorative effect of said serotonin 5-HT3 antagonist on the vestibule allows defining the therapeutic window that will be used in future clinical tests.

Figure 3:
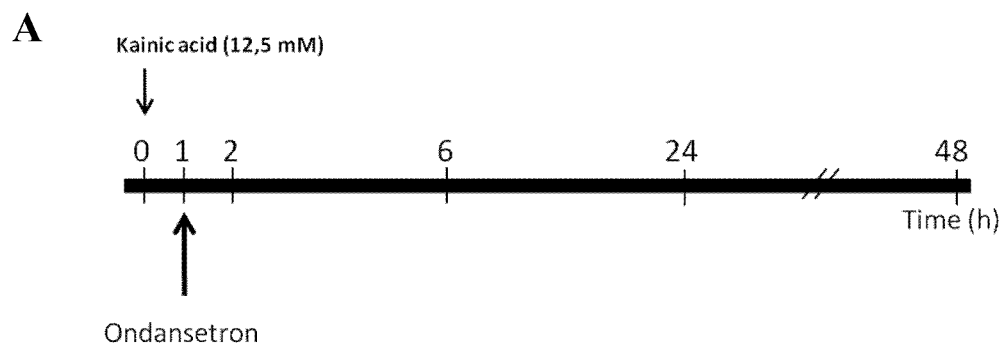
Figure 3:
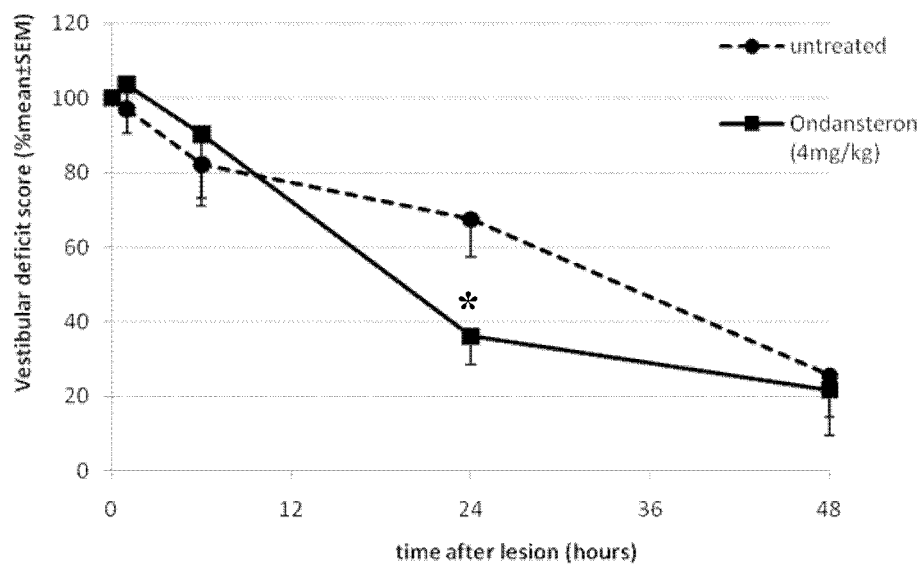
Figure 4:
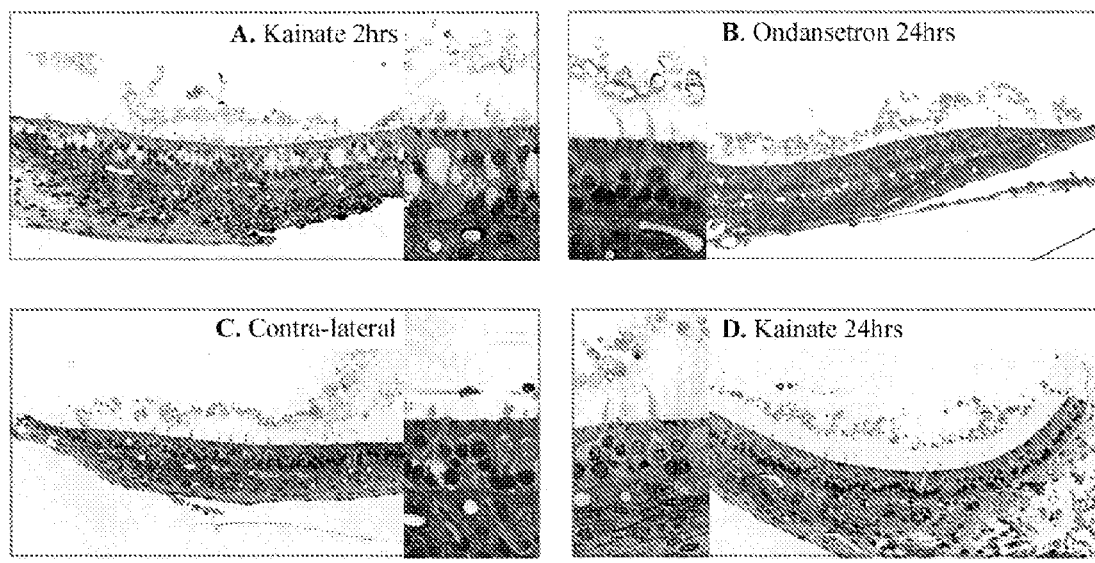

Unilateral Vestibular Deficits (FIGS. 3-5)

Validation of the restorative effect of said serotonin 5-HT3 antagonist is assessed by analysing the time course of arrival and removal of both excitotoxic lesions and ensuing vestibular deficit that occur within vestibular endorgans during intra auricular application of glutamate agonists. In the vestibular endorgans, massive application of kainic acid induces excitotoxic impairments of the neuronal network in the sensory organs (swelling of terminals that contact hair cells—Brugeaud et al., 2007). Histological studies of the expansion and reduction of excitotoxic lesions are undertaken using light and electron microscopy. Behavioural evaluation of vestibular deficit is undertaken using specific behavioural tests of the vestibular function. Under the paradigm developed in the rat, transtympanic application of kainic acid allows its diffusion into the inner ear. In most cases, excitotoxic lesions culminate after 12 h, and disappear within 2-3 days. Protection is investigated following administration of said serotonin 5-HT3 antagonist by intraperitoneal injection of said serotonin 5-HT3 antagonist 1 hour after the kainic acid insult.

Methods:

Induction of Unilateral Vestibular Deficit

Kainic acid (KA), a glutamatergic agonist, was injected transtympanically into the middle ear, after which it diffuses through the round window to the inner ear (vestibule and cochlea) where it acts on afferent nerve fibers. This emulates pathologically occurring, excitotoxic injury mechanisms leading to vestibular deficits. We evaluate the effect of KA injection using behavioral testing of vestibular deficits and histological quantification of the induced lesion.

Ondansetron was Injected Intraperitoneally (ip) at 4 mg/kg (FIG. 3A).

1 h after KA injection, vestibular behavior of the animals was tested followed by ondansetron injection in the treatment group. Control animals did not receive an ondansetron injection. Subsequently, the animals were tested at 2 h, 6 h, 24 h and 48 h after KA injection. Histological and morphometric analysis were performed at 2 and 24 hours after KA injection in the presence and absence of ondansetron treatment.

Behavioral Evaluation of Vestibular Deficit

Vestibular rating score was estimated as previously described (Brugeaud et al., 2007; Boadas-Vaello et al. 2005). Animals were scored from range 0 to 4, respectively corresponding to normal behavior to maximal vestibular deficit. Rating 1 means that the behavior is not normal but no specific vestibular deficit is effectively determined; rating 2 corresponds to an identified but slight vestibular deficit and, rating 3 describes an identified and evident deficit. Six different tests were sequentially scored and totalized to rate the vestibular deficit: 1—the head bobbing, when abnormal intermittent backward extension of the neck was observed; 2—the circling stereotyped movement ranging from none to compulsive circles around the animal hips; 3—the retro-pulsion, a typical backward walk reflecting vestibular disturbance; 4—the tail-hanging reflex, that normally induces a normal forelimb extension to reach the ground, results in the ventral bent of the body and grip of the tail when the vestibular deficit is maximal; 5—the contact-inhibition reflex normally leads animal hold to a metal grid in a subpine position to return when their back touch the ground; in case of vestibular deficit with a lack in the body orientation referential, this reflex is abolished, the animal stays griped to the grid in a supine position; 6—the air-righting reflex is necessary for animals to land on their feet when they fall from a supine position; vestibular dysfunction impairs this normal reversal, a maximal deficit leads the animal to land on its back when dropped from a height of 40 cm onto a foam cushion. Vestibular rating scores were expressed for each time point as a percentage of the t0 score.

Histological Evaluation of Vestibular Lesions

Preparation of semi-thin sections of sensory epithelia. We anesthetized female adult rats (Wistar; 200-220 g; n=3 for each treatment) with pentobarbital (0.4%). Animals were perfused transcardially with heparin PBS (0.01M) followed by a fixative solution (2% paraformaldehyde, 2.5% glutaraldehyde 1% picric acid, 5% sucrose) and samples post-fixed. We embedded vestibular epithelia in Whole vestibular organs were postfixed in 2% $OsO_4$, dehydrated, embedded in Araldite, and 1 μm thick sections were cut. A Nanozoomer Slide Scanner (RIO imaging, Montpellier, France) allowed the observation and scanning of samples mounted on slides.

Scans of semi-thin sections acquired with the Nanozoomer Slide Scanner were analyzed. Quantification of hair cells in utricles was done with Metamorph software (Universal Imaging). For each lesioned and contralateral ear, 3 sections distant of 20 to 25 μm each were analyzed. Thus, 400 cells for each epithelium were counted for each treatment on 3 different animals with the contralateral ear as pooled control. Cells were counted as 1) type I hair cell when a pear shaped cell was observed with its surrounding calyx; 2) type II hair cell when an elongated cell with a highly positioned nucleus was observed; 3) Not-determined type hair cell when the swelled synaptic terminal around the cell prevents from determining a cell type based on its shape, when the calyx was not seen around a pear-shaped cells, when an elongated cell has a nucleus in a low position; 4) supporting cells forming the basal part of the epithelium. ANOVA was used to search for statistical difference, followed by Tukey Test to compare between treatments.

Results:

Following transtympanic kainic acid injection, rats exhibit strong excitotoxically induced vestibular deficits which gradually decrease in 48 hours (FIG. 3B). This time course of decreased vestibular deficits is altered when animals are treated with ondansetron, with significantly reduced vestibular deficits at 24 hours (*p=0.022; Mann Whitney test; n≥8). Subsequently, both treated and untreated animals recover to similar vestibular deficit levels due to endogenous compensatory mechanisms.

As shown in FIG. 4A, KA induces a large exocytotic lesion of the vestibular afferents in the sensory epithelia 2 hrs after its transtympanic injection (FIG. 4A). In comparison to the contra-lateral not-lesioned ear (FIG. 4C), large swelled synaptic endings were observed along hair cells instead of the typical calyceal-type I and bouton-type II nerve endings. When observed 24 hrs after the lesion, newly calyceal and boutons endings were observed with (FIG. 4B) and without (FIG. 4D) Ondansetron. At the photonic microscopic level, Ondansetron seemed to potentiate the maturation of these "neo-formed" synaptic terminals.

As shown in FIG. 5, morphometric analysis determined that no loss of hair or supporting cells was induced by the transtympanic injection of KA. In reverse, the number of identified type I hair cells with their surrounding calyx was largely and significantly reduced by KA (P<0.001), confirmed by the increased number of not-determined hair cell cells (P<0.01). When counted 24 hrs after the exocytotic injury, the number of type I hair cells newly identified was significantly increased (p<0.01), but the number of not-determined hair cells not significantly reduced. This result proved the capacity of synaptic terminals to repair after exocytotic injury. For Ondansetron treatment as well, we observed a significantly increased number of type I hair cells 24 hrs after the KA lesion (p<0.01). More interestingly, the number of not-determined hair cells was significantly reduced by the ondansetron treatment (P<0.01) reflecting a protection or/and facilitation of the repair for the exocytotic injured synaptic terminals.

Present behavior observations that the kainate-induced vestibular deficits are significantly reduced (24 h following the excitotoxic insult) upon treatment with ondansetron, can be interpreted either by a prevention of the lesions extension or a potentiation of the recovery processes in the treated rats. In any cases, it can be postulated that the better vestibular state observed in the ondansetron-treated animals is supported by a better efficiency of the vestibule function. Histological observations support the idea that hair cell branching pattern is either better preserved or better repaired in the treated animals.

Figure 6:
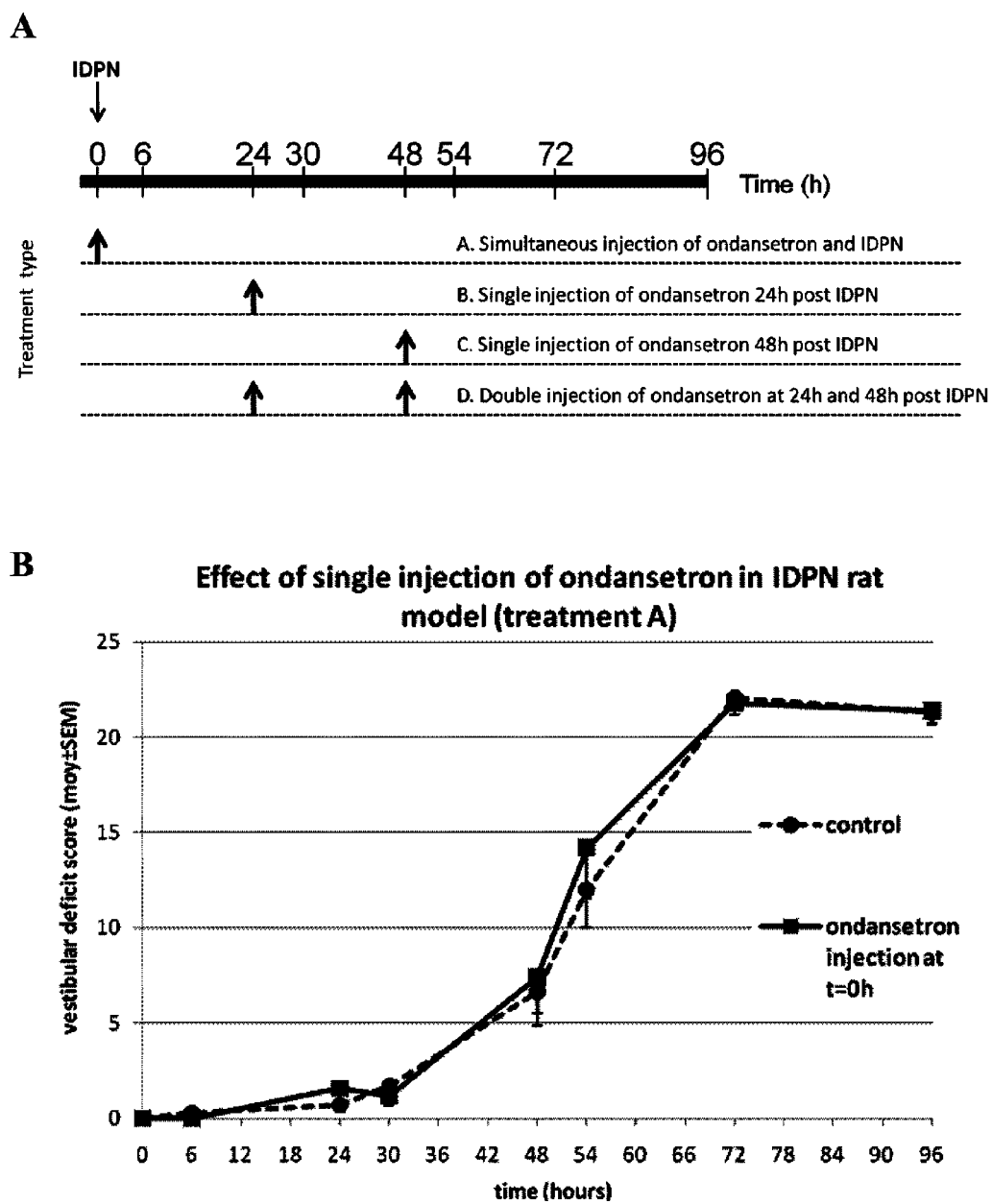
Figure 6:
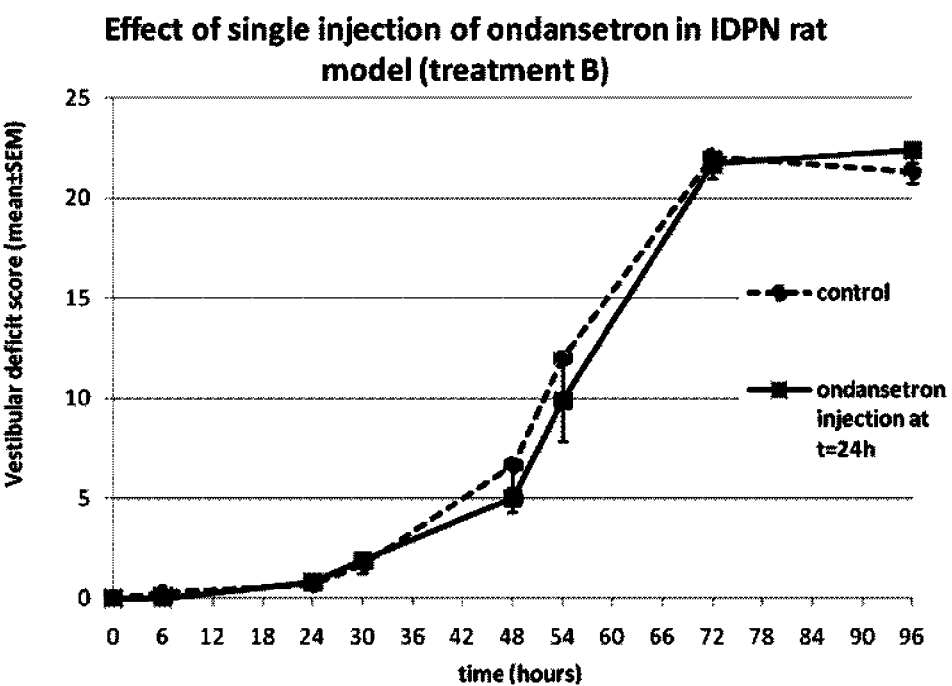
Figure 6:
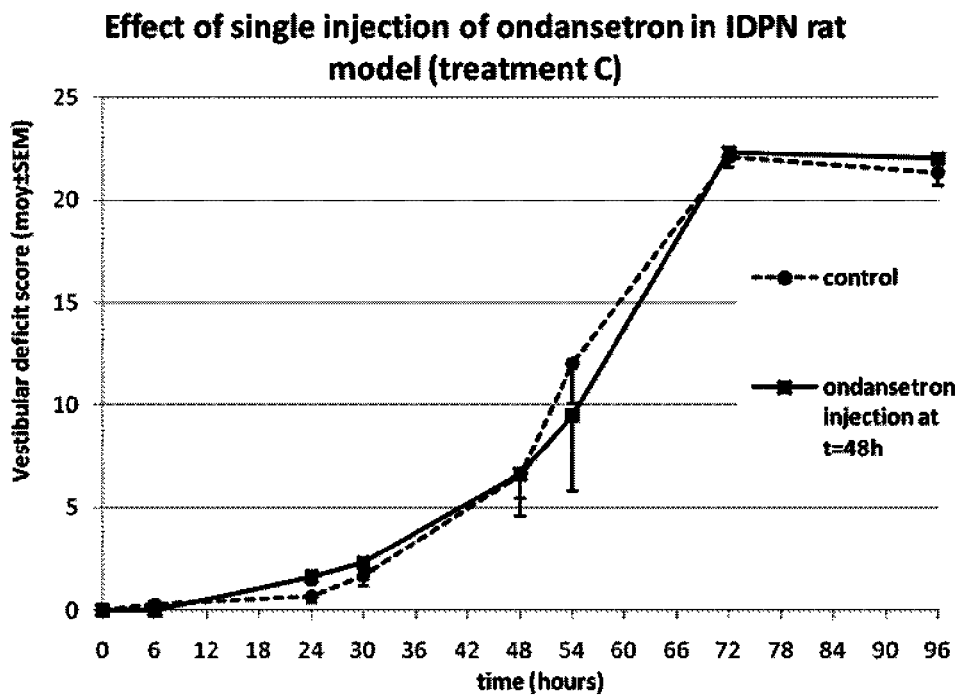
Figure 6:
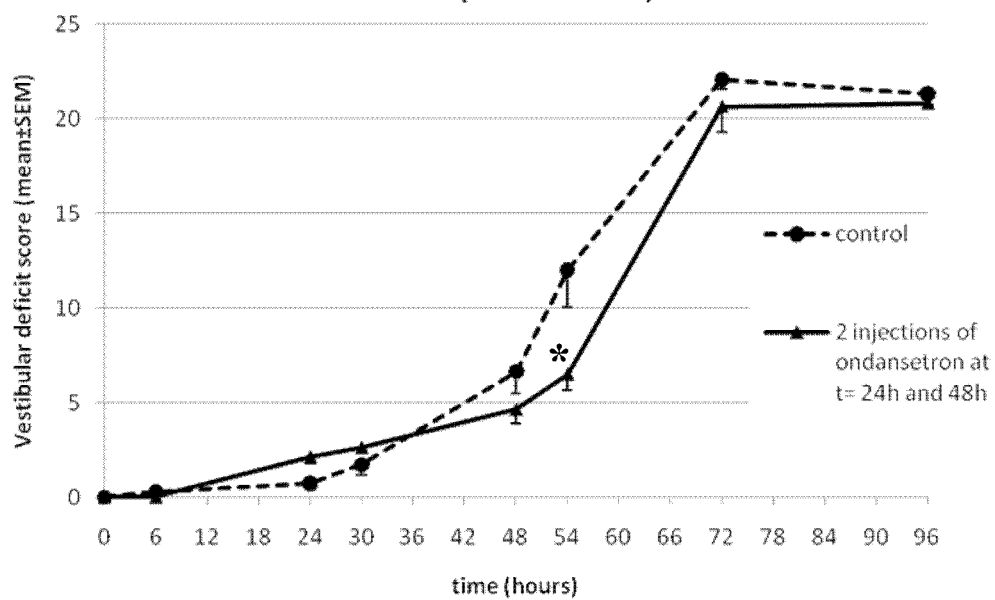

Bilateral Vestibular Deficits (FIG. 6)

Validation of the restorative effect of said serotonin 5-HT3 antagonist is also assessed on animal model of bilateral vestibular deficit by analysing the time course of arrival and removal of both excitotoxic lesions and ensuing vestibular deficit following intoxication with nitriles (IP injection—Seoane et al., J. Comp. Neurol. 2001, 439:385-399). Following their metabolization nitriles induces ototoxic/excitotoxic damages and vestibular deficits identifiable within 3 days following their acute application. Protection is assessed by administration of said serotonin 5-HT3 antagonist following different schedules (at the start of chronic intoxication; 24 and 48 h after).

Methods:

IDPN (1 g/kg; ip) induces bilateral and permanent vestibular damage through destruction of the vestibular sensory epithelium. This progressive injury reaches its maximal extent after 72 hours. We assessed the effect of IDPN injection using behavioral testing of vestibular deficits. We evaluated the protective effect of single or double injections of ondansetron throughout the time course of injury progression following IDPN injection to determine the vestibuloprotective potential of ondansetron. Each dose of ondansetron was injected intraperitoneally (ip) at 4 mg/kg.

We used 4 treatment paradigms (FIG. 6A):

A. Simultaneous injection of ondansetron (1 dose) and IDPN.
B. Injection of ondansetron (1 dose) 24 hours after IDPN injection.
C. Injection of ondansetron (1 dose) 48 hours after IDPN injection.
D. 2 injections of ondansetron (total of 2 doses) 24 h and 48 h after IDPN injection.

Behavioral testing was performed at 6, 24, 30, 48, 54, 72 and 96 hours after IDPN injection.

Results:

The time course of increasing vestibular deficits is not significantly altered when animals received ondansetron simultaneously with IDPN (p≤0.05 Mann Whitney test; n≥5) (FIG. 6B).

The time course of increasing vestibular deficits is not significantly altered when animals are treated with ondansetron, 24 h after the IDPN injection (p≤0.05 Mann Whitney test; n≥7) (FIG. 6C).

The time course of increasing vestibular deficits is not significantly altered when animals are treated with ondansetron 48 h after IDPN injection (p≤0.05 Mann Whitney test; n≥6) (FIG. 6D).

Ondansetron was injected 24 and 48 hours (2 doses) after vestibular deficit induction with IDPN (t=0 h). Behavioral testing has shown a significant modification of the time course of increasing vestibular deficit at 54 h (p≤0.05 Mann Whitney test; n≥7). Animals treated with ondansetron at 24 and 48 h shown significantly less severe vestibular deficits at 54 h following the second ondansetron injection (FIG. 6E).

Present behavior observations that nitrile-induced vestibular deficits are significantly reduced (24 and 48 h following the toxic insult) upon treatment with ondansetron, can be interpreted by an early prevention of the lesions extension, rather than a potentiation of the recovery processes in the treated rats. Indeed, nitriles kill the hair cells within 3 days therefore preventing any reconnection of the nerve afferents as postulated to occur in the kainate-treated animals. In any cases, it can be postulated that the better vestibular state observed in the ondansetron-treated animals is supported by a better efficiency of the vestibule function. Future histological investigations will allow determining whether hair cell branching pattern is better preserved at 24 h-48 h after the nitrile insult in the treated animals.

Example 4

Examples of Composition Comprising Ondansetron for Nasal Administration

|  | Composition 1 | Composition 2 | Composition 3 |
|---|---|---|---|
| Ondansetron base | 8 mg/ml | 10 mg/ml | 6 mg/ml |
| Sodium chloride | 0.9% | 0.9% | 0.9% |
| Potassium sorbate | 0.125% | 0.125% | 0.125% |
| citrate | qsp pH 4.5 | qsp pH 4.5 | qsp pH 4.5 |
| Purified water | Qsp | Qsp | qsp |

Stability of Solution Comprising Ondancetron Base

A solution comprising about 8 mg/ml of ondansetron base was found to be physically stable after 1 month storage at 25° C. and 1 month storage at 4° C.

Chemical stability of the solution was also assessed:

| Tests | Specifications | T0 | T = 1 month at 25° C. | T = 1 month at 4° C. |
|---|---|---|---|---|
| Aspect of the solution | Clear | clear | clear | clear |
| Coloration | > or = JB7 | ok | ok | ok |
| pH | 3.30-4.5 | 4.44 | 5.35 | 4.95 |
| Particles | | | | |
| > or = 10 µM | < or = 6000/bottle | 52 | 338 | 65 |
| > or = 25 µm | < or = 600/bottle | 5 | 75 | 10 |
| dosage | 95-105% | 100% | 101.4% | 102.9% |
| Total impurities | < or = 0.5% | 0.02% | 0.12% | 0.13% |

These observations show that pH modification is not associated to significant chemical degradation of ondansetron. No precipitation can be observed. Stabilization of the pH can be realized by using a citrate buffer.

REFERENCES

Throughout this application, various references describe the state of the art to which this invention pertains. The disclosures of these references are hereby incorporated by reference into the present disclosure.

Brugeaud A, Travo C, Dememes D, Lenoir M, Llorens J, Puel J L, Chabbert C. Control of hair cell excitability by vestibular primary sensory neurons. J Neurosci. 2007; 27(13):3503-11.

Gil-Loyzaga P, Bartolomé M V, Vicente-Torres M A. Serotonergic innervation of the organ of Corti of the cat cochlea. Neuroreport. 1997;8(16):3519-22.

Johnson D S, Heinemann S F. Embryonic expression of the 5-HT3 receptor subunit, 5-HT3R-A, in the rat: an in situ hybridization study. Mol Cell Neurosci. 1995; 6(2):122-38.

Seoane A, Demêmes D, Llorens J. Relationship between insult intensity and mode of hair cell loss in the vestibular system of rats exposed to 3,3'-iminodipropionitrile. J Comp Neurol. 2001; 439(4):385-99.

Turconi M, Nicola M, Quintero M G, Maiocchi L, Micheletti R, Giraldo E, Donetti A. Synthesis of a new class of 2,3-dihydro-2-oxo-1H-benzimidazole-1-carboxylic acid derivatives as highly potent 5-HT3 receptor antagonists. J Med Chem. 1990 August; 33(8):2101-8.

The invention claimed is:

1. A method of treating a lesional vestibular disorder in a subject in need thereof comprising:
   administering an effective amount of a serotonin 5-HT3 receptor antagonist to a subject having a lesional vestibular disorder.

2. The method of claim 1, wherein the serotonin 5-HT3 receptor antagonist is a small organic molecule, antibody, or aptamer.

3. The method of claim 2, wherein the serotonin 5-HT3 receptor antagonist is ondansetron, palonosetron, tropisetron, lerisetron, alosetron, granisetron, dolasetron, bernesetron, ramosetron, azasetron, itasetron, zacopride, or cilansetron.

4. The method of claim 3, wherein the serotonin 5-HT3 receptor antagonist is ondansetron.

5. The method of claim 2, wherein the serotonin 5-HT3 receptor antagonist is a compound, physiologically acceptable salt, or physiologically acceptable solvate of formula (I):

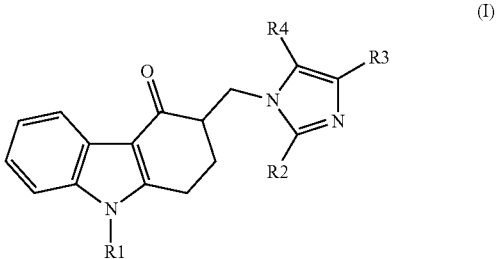

(I)

wherein:
R1 represents a $C_{3-7}$ cycloalkyl-$(C_{1-4})$ alkyl group or a $C_{3-10}$ alkynyl group; and
one of the groups represented by R2, R3 and R4 is a hydrogen atom or a $C_{1-6}$ alkyl, $C_{3-7}$ cycloalkyl, $C_{2-6}$ alkenyl or phenyl-$(C_{1-3})$ alkyl group and each of the other two groups, which may be the same or different, represents a hydrogen atom or a $C_{1-6}$ alkyl group.

6. The method of claim 1, further defined as comprising administering an effective amount of the serotonin 5-HT3 receptor antagonist nasally.

7. The method of claim 6, further comprising obtaining a device adapted for nasal administration of the 5-HT3 receptor antagonist and using the device to administer the 5-HT3 receptor antagonist to the subject.

8. The method of claim 1, wherein the vestibular deficit is vestibular neuritis, viral neuronitis, labyrinthitis, viral endolymphatic labyrinthitis, drug-induced ototoxicity, Ménière's disease, endolymphatic hydrops, head trauma with a lesional vestibular deficit, labyrinthine haemorrhage, chronic or acute labyrinthine infection, serous labyrinthine, barotraumatism, autoimmune inner ear disease, chronic Ménière's disease, presbyvestibulia, or a toxic vestibular impairment.

9. The method of claim 1, wherein the subject is a human.

10. The method of claim 1, wherein the vestibular disorder is vestibular neuritis, viral neuronitis, labyrinthitis, viral endolymphatic labyrinthitis, drug-induced ototoxicity, head trauma with a lesional vestibular deficit, labyrinthine haemorrhage, chronic or acute labyrinthine infection, serous labyrinthine, barotraumatism, autoimmune inner ear disease, presbyvestibulia, or a toxic vestibular impairment.

* * * * *